United States Patent
Staud

(10) Patent No.: US 9,795,403 B2
(45) Date of Patent: Oct. 24, 2017

(54) MEDICAL GRIPPING TOOL

(75) Inventor: Ralf Staud, Emmingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 938 days.

(21) Appl. No.: 13/150,957

(22) Filed: Jun. 1, 2011

(65) Prior Publication Data

US 2011/0295314 A1 Dec. 1, 2011

(30) Foreign Application Priority Data

Jun. 1, 2010 (DE) .................. 10 2010 022 431

(51) Int. Cl.
| | | |
|---|---|---|
| A61B 17/00 | (2006.01) | |
| A61B 17/29 | (2006.01) | |
| A61B 18/14 | (2006.01) | |
| A61B 18/00 | (2006.01) | |

(52) U.S. Cl.
CPC .......... *A61B 17/29* (2013.01); *A61B 18/1445* (2013.01); *A61B 2017/00345* (2013.01); *A61B 2017/00995* (2013.01); *A61B 2017/2926* (2013.01); *A61B 2018/00125* (2013.01); *A61B 2018/00148* (2013.01)

(58) Field of Classification Search
CPC ..... A61B 17/28–17/29; A61B 18/1445; A61B 2017/00345; A61B 2017/00995; A61B 2017/2926; A61B 2018/00148; A61B 17/00; A61B 17/30; A61B 17/221; A61B 17/2421; A61B 17/22031
USPC .................... 606/1, 205, 207, 208; 74/490.05
See application file for complete search history.

(56) References Cited

U.S. PATENT DOCUMENTS

| | | | |
|---|---|---|---|
| 4,274,413 A | | 6/1981 | Hahn et al. |
| 5,147,378 A | * | 9/1992 | Markham ............... 606/206 |
| 5,638,827 A | * | 6/1997 | Palmer et al. ......... 600/564 |
| 5,746,770 A | * | 5/1998 | Zeitels et al. .......... 606/207 |
| 6,059,783 A | * | 5/2000 | Kirwan, Jr. ............. 606/51 |
| 7,377,920 B2 | * | 5/2008 | Buysse et al. .......... 606/46 |
| 7,628,792 B2 | * | 12/2009 | Guerra .................... 606/51 |
| 7,935,052 B2 | * | 5/2011 | Dumbauld .............. 600/205 |
| 2003/0069571 A1 | * | 4/2003 | Treat ............. A61B 18/085 |
| | | | 606/29 |
| 2003/0158549 A1 | * | 8/2003 | Swanson ................. 606/41 |
| 2003/0171748 A1 | | 9/2003 | Truckai et al. |
| 2010/0159260 A1 | * | 6/2010 | Elia et al. ............... 428/458 |
| 2010/0263500 A1 | * | 10/2010 | Bannasch ...... A61B 17/0206 |
| | | | 81/487 |

(Continued)

FOREIGN PATENT DOCUMENTS

| | | |
|---|---|---|
| DE | 20318845 U1 | 3/2004 |
| DE | 69832497 T2 | 8/2006 |

(Continued)

OTHER PUBLICATIONS

European Search Report; Application No. EP 11 16 5953; Issued: Sep. 12, 2011; 7 pages.

*Primary Examiner* — Victor Nguyen
(74) *Attorney, Agent, or Firm* — Whitmyer IP Group LLC

(57) ABSTRACT

A medical gripping tool includes a synthetic body and a metallic layer on a surface of the synthetic body, whereby the synthetic body is configured to be elastically reshaped in its expected application. According to the invention, the gripping tool is configured so that the metallic layer is structurally reshaped in the expected application.

15 Claims, 4 Drawing Sheets

(56) References Cited

U.S. PATENT DOCUMENTS

2010/0298864 A1* 11/2010 Castro .......................... 606/205

FOREIGN PATENT DOCUMENTS

| DE | 202007009310 U1 | 8/2007 |
| --- | --- | --- |
| DE | 102007026721 A1 | 5/2008 |
| DE | 102007050018 A1 | 5/2008 |
| EP | 1201198 A1 | 5/2002 |

* cited by examiner

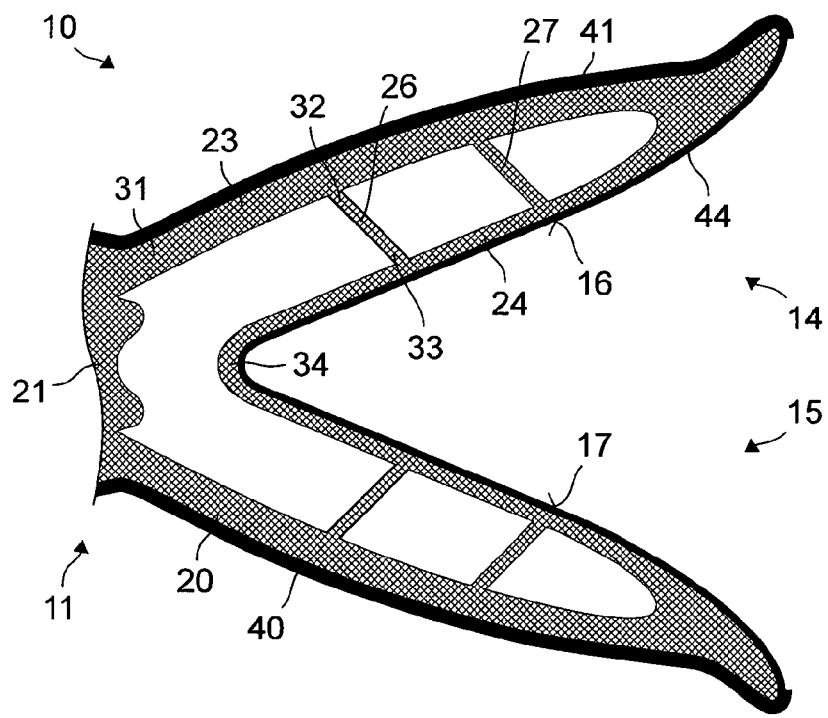
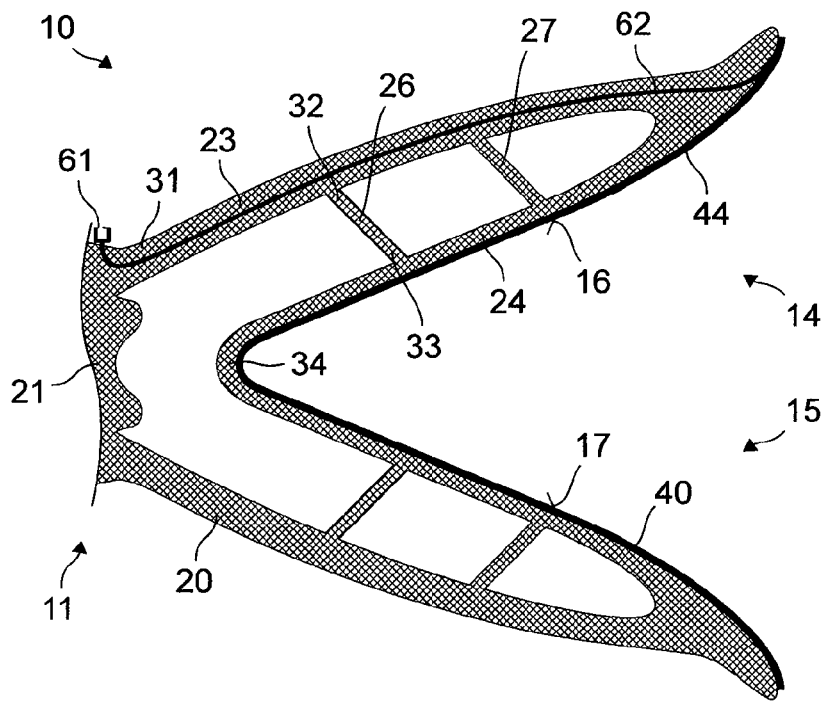

MEDICAL GRIPPING TOOL

CROSS-REFERENCE TO RELATED APPLICATIONS

The present application claims priority of German patent application No. 10 2010 022 431.6 filed on Jun. 1, 2010, the content of which is incorporated herein by reference.

FIELD OF THE INVENTION

The present invention relates to a medical gripping tool, in particular for micro-invasive operations, with a synthetic body and a metallic layer on a surface of the synthetic body, whereby the synthetic body is configured to be reshaped in the course of its expected use. In addition, the present invention relates to a method for handling a medical object, in particular in a micro-invasive operation, with the following steps: positioning on the medical object a medical gripping tool with a synthetic body and a metallic layer on a surface of the synthetic body; and reshaping the medical gripping tool in order to grip the medical object so that the synthetic body is reshaped. A gripping tool of this type and a method of this type are known from invention DE 20 2007 009 310 U1.

BACKGROUND OF THE INVENTION

In medical operations, it is often not possible to grip and/or hold vessels, organs, tissue or other medical objects in a direct manual manner. This applies especially for micro-invasive operations. In these cases, gripping tools are used. Such tools constitute forceps-type instruments in a wider sense. For various applications, in particular tissues of different mechanical properties and different sensitivity, a broad range of different medical gripping tools is available to make possible a gripping or holding that is simultaneously secure and protective or atraumatic.

Newer developments aim at using synthetic for medical gripping tools. In particular in injection-molding methods, gripping tools can be produced in synthetic rapidly and in great number at reasonable cost. The greater elasticity of synthetic, especially in comparison with metals often used conventionally, makes possible to some extent a fundamentally different design. For example, solid-state joints can be provided.

In patents DE 10 2007 026 721 A1 and DE 10 2010 009 259.2, shape-adapting medical gripping tools are described that are based on the fin-ray effect. The aforementioned patent DE 10 2007 026 721 A1 also discloses a gripping layer that is coated with micro- or nano-particles, which are not specified in further detail. Patent DE 10 2007 050 018 A1 discloses a medical gripping tool with spring elements in fluid chambers or for the support of gripping surfaces. Patent DE 698 32 497 T2 describes a medical gripping tool with a gripping layer that is coated with metallic granules that are not joined together.

For some applications, however, medical gripping tools made of synthetic have insufficient mechanical solidity. For example, medical gripping tools of synthetic, when required to transmit torque onto the medical object that is being held, show an undesired reshaping, in particular a torsion that cannot be reduced or eliminated except at considerable construction cost.

SUMMARY OF THE INVENTION

It is an object of the present invention to provide an improved medical gripping tool and an improved method for handling a medical object.

Embodiments of the present invention are based on the idea of providing a medical gripping tool with a synthetic body and with a metallic layer on a surface of the synthetic body. Metallic layers on surfaces of synthetic bodies are already known from various fields in the art. There, they originally served mainly decorative purposes. Cost-effective production of injection-molded parts is meant to be combined with the assumption of a metallic component. A mechanical impact leads as a rule to tearing and chipping away of the metallic layer. Particles released by a medical instrument, however, constitute a considerable health risk for patients. It is therefore unthinkable in conventional terms to have a medical gripping tool with a synthetic body that is configured to be elastically reshaped in the expected application, and a metallic layer on a surface of the synthetic body.

It was known, however, that more recent technologies in the meantime make possible a development and configuration of the synthetic body and of the metallic layer on its surface, both of which can prevent, with sufficient certainty, tearing and chipping away of the metallic layer even with repeated, extensive elastic or structural reshaping of the synthetic body and with structural reshaping of the metallic layer. Thus, for the first time, the advantages of the low production costs and of the elasticity of synthetic bodies can be used for medical gripping tools.

The aforementioned reshaping of the synthetic body is not merely a minor reshaping as occurs in particular in solid-state joints. This reshaping can be purely elastic or else partly elastic and partly structural. This does not mean a minor reshaping such as is unavoidable in impacts to every actual component.

The synthetic body can be produced at reasonable cost, for example by the injection-molding method. The metallic layer on its surface, depending on its properties and its manufacturing method, can also be obtained economically. The medical gripping instrument can thus involve such low overall production costs that it can be adopted for one-time use followed by disposal. This dispenses with the need for effort and costs for cleaning and sterilizing the gripping tool after each use.

Because of the elastic reshapability of the synthetic body, it is possible to dispense with conventional joints with shafts and bearings, for example, that involve high production costs for conventional gripping tools made of metal. Owing to high production costs of conventional gripping tools made of metal, such tools need to be used multiple times and cannot be discarded or recycled after just one use. However, these same conventional joints with shafts and bearings show abrasion and can become stiff or jammed from dirt. Often such problems can be avoided only at considerable expense in design and production.

The metallic layer on the surface of the synthetic body makes certain defined mechanical properties possible. In particular, with the metallic layer it is possible to achieve a high degree of mechanical stability, which can reduce torsion of the gripping tool to an acceptable quantity, also for example when torque is in effect. Sufficient mechanical stability can thus be achieved even with markedly smaller cross-sections on the synthetic body. The medical gripping tool can therefore be configured in markedly thinner or smaller format, for example, in some cases with equal gripping force.

In the case of the inventive medical gripping tool, the metallic layer is configured to be structurally reshaped in the expected application.

Repeated structural reshaping of a metal can lead to fracturing from brittleness. This can occur, however, to a markedly lesser extent with a metallic layer with a granular size of 100 nm or less, and to an even lesser extent with granular sizes of 30 nm or less (in particular, 10 nm to 20 nm). Thus it is possible for the medical gripping tool, the synthetic body and the metallic layer on its surface, for example, to be of such dimensions and/or such configuration that in the expected application, for example in the area of a solid-state joint, the synthetic body is reshaped elastically and the metallic layer on its surface is reshaped structurally. The metallic layer can thus simultaneously, on the one hand, increase the mechanical stability of the medical gripping tool and, on the other hand, make possible a configuration of solid-state joints without the risk of tearing or chipping away.

The metallic layer can consist of a single layer or can include a multi-layered system. Two-layered systems have proven themselves in the art with combinations and alloys of bromine, cobalt, molybdenum, nickel, chrome, gold, carbon, copper, palladium, phosphor, platinum, silver, sulfur, titanium, tungsten, tin, iron as well as oxides of these elements. The metallic layer or individual layers of a multi-layered system can each be microscopically homogeneous or can comprise a matrix with metallic or other particles embedded in it. In this case the matrix and the particles embedded in it comprise different materials. The particles embedded in the matrix, in particular, likewise have sizes of at most 100 nm or at most 30 nm (in particular, 10 nm to 20 nm). The particles can likewise comprise combinations or alloys of the aforementioned elements.

In a medical gripping tool as described here, the synthetic body includes in particular a first gripping member, a second gripping member and a solid-state joint between the first and second gripping members.

In this embodiment of the medical gripping tool, the aforementioned advantage of elasticity of the synthetic comes into play. While conventionally at least two gripping members and a shaft would have to be produced separately and then assembled, only one part needs to be produced here, and the assembly step can be dispensed with. The production costs, which as mentioned are comparatively low in any case, can be still further reduced. This makes it advantageous to configure the medical gripping tool for one-time use and subsequent disposal.

In a medical gripping tool as described here, at least either the first gripping member or the second gripping member can comprise a beam structure.

In a beam structure, a gripping member comprises several beams or studs and/or beam- or stud-shaped portions. Said beams and studs can each be either straight or curved and can comprise constant or varying cross-sections. Each set of three or four rods or studs can form a triangle or quadrilateral.

By means of the beam structure it is possible to obtain defined mechanical properties, which can be selected within broad boundaries, at comparatively low mass, in particular a particularly high rigidity or a defined elasticity. Both the rigidity and the elasticity of the beam structure can be selectively influenced by the metallic layer. For this purpose the metal layer can comprise different layer thicknesses and/or different materials and/or different layer structures in different areas of the medical gripping tool. In addition, individual areas can be coated in order to increase their rigidity while one or more other areas are not coated, in order to maintain the elasticity of the synthetic body locally without reduction.

In a medical gripping tool as described here, at least either the first gripping member or the second gripping member can be configured to be reshaped during gripping of an object in accordance with the fin-ray effect.

The fin-ray effect is the English term for this effect in the art. Similar medical gripping tools are described in patents DE 10 2007 026 721 A1 and DE 10 2010 009 259.2. A gripping tool that is based on the fin-ray effect has the particular advantage of defined and differentiated mechanical properties, as well as mechanical properties that vary from site to site within the gripping tool.

Even a metallic layer on the synthetic body that is homogeneous with respect to its thickness and other properties can cause a marked improvement in this respect. The metal of the metallic layer as a rule comprises a markedly lower elasticity than the synthetic of the synthetic body. Because the metallic layer on the surface of the synthetic body, for example in the case of a stud or beam, is at the maximum distance from the neutral fiber of the beam, said layer has considerable influence on the pliability of the beam. The cross-section of the beam, in particular the distance of the beam surface from the neutral fiber, therefore has a pronounced influence on the pliability of the beam when the described metallic layer is placed on the surface. In the case of solid-state joints with locally reduced cross-section, for example, the elastic reshaping is therefore still more strongly localized in the area of the reduced cross-section when a metallic layer is provided on the surface. The possibility of localizing the reshaping even more strongly at a solid-state joint by means of the metallic layer allows an even better definition of the kinematic properties of the medical gripping tool.

An additional improvement is possible if the metallic layer comprises a varying thickness or another varying property or is not present at all, for example, in the area of the solid-state joints.

In a medical gripping tool as described here, the metallic layer has in particular an average granular size of at most 100 nm.

The average granular size is the average size of the crystallites of the polycrystalline metallic layer. Because crystallites of the polycrystalline metallic layer, at least in exceptional cases, are of approximately spherical shape, the size of a crystallite is taken to be the equivalent diameter of the crystallite. The equivalent diameter in this case is the length of one edge of a quadratic hole of a grid through which the crystallite can just barely pass.

At an average granular size of at most 100 nm, many metals comprise a markedly increased ductility in comparison with customary granular sizes, which are greater by several orders of magnitude. The risk of tearing or chipping away of the metallic layer is thus markedly reduced. Especially good results are achieved at an average granular size of at most 30 nm, in particular at average granular sizes of 10 nm to 20 nm. An average granular size of at most 100 nm, and even more an average granular size of at most 30 nm or of 10 nm to 20 nm, is particularly suited for the aforementioned configurations of the medical gripping tool in which the metallic layer is structurally reshaped in the expected application. The particular suitability stems primarily from the fact that the particularly high ductility can prevent tearing and chipping away of the metallic layer at repeated strong reshaping, for example in the area of a solid-state joint.

In a medical gripping tool as described here, the metallic layer can be present on a gripping surface of the gripping tool.

In particular, the metallic layer is exclusively, or essentially exclusively, present on one or both gripping surfaces of the gripping tool. An electrically conductive metallic layer on a gripping surface of the gripping tool can make possible an electrical functioning of the gripping tool. For example, a high-voltage alternating current of appropriate voltage and amplitude can be applied on the metallic layer on the gripping surface of the gripping tool in order to obliterate or sever tissue by coagulation.

In a medical gripping tool as described here, it is possible on a gripping surface of the gripping tool to provide no metallic layer or a thinner metallic layer than at other areas of the surface of the gripping tool.

Owing to the fact that no metallic layer or only a thin metallic layer is present on a gripping surface of the gripping tool, the elasticity of the synthetic body in the area of the gripping surface can remain completely or largely intact. This can promote a protective or atraumatic gripping of tissue. In addition, the friction between the synthetic surface of the synthetic body and tissue can be greater than that between a metallic layer and tissue.

A medical gripping tool as described here can be configured, for example, as a needle holder. The metallic layer makes possible a sufficiently rigid configuration of the needle holder in order to make possible the transmission of great forces onto the needle. At the same time, a gripping surface of the needle holder that is not provided with the metallic layer can make possible a good force lock or friction lock between the needle holder or the synthetic body on the one hand and the needle on the other hand.

The elasticity of the synthetic body on the gripping surface can be partly or predominantly maintained with a thin metallic layer, while electrical function is achieved at the same time.

In a medical gripping tool as described here, at a solid-state joint of the gripping tool it is possible to provide no metallic layer or a thinner metallic layer than at other areas of the surface of the gripping tool.

As already indicated, the metallic layer can markedly reduce the pliability of a portion of the synthetic body, for example a beam-shaped portion. Owing to the fact that in the area of a solid-state joint no metallic layer is present, or a thinner metallic layer is present than at other areas of the surface of the synthetic body, it is possible to maintain the elasticity of the synthetic body to its full extent in the area of the solid-state joint. Because in other areas the metallic layer can markedly reduce the elasticity of the synthetic body, the described configuration of the metallic layer makes possible a markedly good definition or limitation of the solid-state joint and thus also an especially defined kinematics of the medical gripping tool.

A medical gripping tool as described here can, in addition, include a contacting device for electrical contacting of the metallic layer, whereby the metallic layer includes a portion on a gripping surface so that the portion on the gripping surface is connected in electrically conductive manner with the contacting device.

The contacting device is, for example, a solder tail, a plug-in contact or a portion of the metallic layer that can be configured as especially thick. The portion on the gripping surface is configured, in particular, without an oxide layer or other electrically insulating layer. The contacting device and the portion of the metallic layer on the gripping surface are, for example, interconnected directly or by means of a conductor track or wire in electrically conductive manner. The described configuration of the medical gripping tool allows an electrical functioning, for example the severing and/or obliteration of tissue by coagulation.

In a medical gripping tool as described here, the metallic layer can include a nickel layer with an average granular size of at most 100 nm and a copper layer between the synthetic body and the nickel layer.

The advantages of a small average granular size in the metallic layer have already been described and apply in particular to a nickel layer. The copper layer between the synthetic body and the nickel layer makes possible an especially durable and reliable fastening of the nickel layer to the surface of the synthetic body. The copper layer, in particular, comprises an average granular size of at most 100 nm.

In a method for handling a medical object, a medical grip with a synthetic body and with a metallic layer on a surface of the synthetic body is positioned and reshaped on the medical object in order to grip the medical object, so that the synthetic body is reshaped.

According to the present invention, upon reshaping the medical gripping tool the metallic layer is structurally reshaped.

As already described, metal-coated synthetic bodies were customarily configured in the art in such a way that in the expected application a minor elastic reshaping, at most, of the synthetic body occurred to prevent tearing and chipping of the metallic layer. It was recognized, however, that in a suitable configuration of the metallic layer, in particular in the aforementioned small granular sizes, the medical gripping tool can be completely configured so that in the expected application the metallic layer can even be structurally reshaped without risking tearing or chipping of the metallic layer.

The synthetic body comprises, for example, ABS (acrylonitrile-butadiene-styrene), LCP (liquid crystal polymer), PA (polyamide), PC (polycarbonate), PEEK (polyetheretherketone), PEI (polyetherimide), PPA (polyphthalamide), PPS (polyphenylene sulfide) or a mixture of two or more of these synthetic substances, for example a mixture of PC and ABS. The synthetic body can, in addition, comprise reinforcing fibers, for example glass, basalt, boron, ceramic, silicic acid, aramid, carbon, polyester, nylon, polyethylene or plexiglass fibers.

The metallic layer, on the basis of its material, its surface structure or as a result of another antireflecting layer, can be configured in such a way that disturbing bright reflections of the illuminating light on the medical gripping tool are reduced or prevented.

BRIEF DESCRIPTION OF THE DRAWINGS

Embodiments are described in greater detail hereinafter with reference to the appended drawings, which are as follows:

FIG. 3 shows a schematic depiction of another medial gripping tool of an embodiment of the present invention;

FIG. 4 shows a schematic depiction of another medial gripping tool of an embodiment of the present invention;

DETAILED DESCRIPTION OF THE INVENTION

Figure 1:
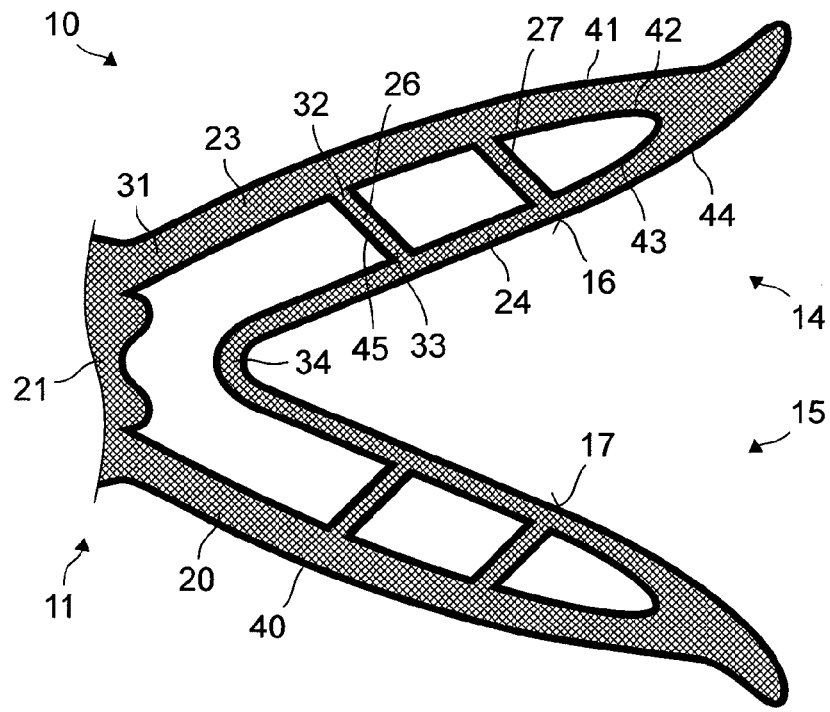
FIG. 1 shows a schematic depiction of a medical gripping tool of an embodiment of the present invention.

FIG. 1 shows a schematic depiction of a section through a medical gripping tool 10. A proximal end 11 of the medical gripping tool 10 is, for example, mechanically connected in (non-destructively) detachable or durable or destructively detachable manner with a distal end of a shaft that is not shown in FIG. 1. The medical gripping tool 10 includes a first gripping member 14 and a second gripping member 15, which are interconnected at the proximal end 11 of the medical gripping tool.

Each of the gripping members 14, 15 comprises a gripping surface 16, 17. The gripping surface 16 on the first gripping member 14 faces toward the second gripping member 15, while the gripping surface 17 on the second gripping member 15 faces toward the first gripping member 14. As described hereinafter, the gripping members 14, 15, starting from the position shown in FIG. 1, can be moved toward one another until the gripping surfaces 16, 17 touch one another.

The medical gripping tool includes a synthetic body 20, so that the first gripping member 14 and the second gripping member 15 each include a portion of the synthetic body 20. The first gripping member 14 includes an external beam 23 and an internal beam 24 of the synthetic body 20, which transition into one another distally. Reference is made hereinafter, using the terms "external" and "internal," to distinguish marks or sides that are turned away from the gripping surfaces 16, 17 or face toward the gripping surfaces 16, 17.

A first stud 26 and a second stud 27 are positioned between the external beam 23 and the internal beam 24 of the first gripping member 14. The first stud 26 and the second stud 27 are parallel or essentially parallel to one another. The first stud 26 and the second stud 27 can each be positioned perpendicular to the external beam 23 and to the internal beam 24 of the first gripping member 14 or, as shown in FIG. 1, at a different angle.

The second gripping member 15 can be configured as a mirror image, or essentially as a mirror image, of the first gripping member 14 and consequently is not described in further detail hereinafter. The external beam 23 of the first gripping member 14 and the corresponding external beam of the second gripping member 15 continue on the proximal end 11 of the gripping tool 10 into a proximal end 21 of the synthetic body 20, by which they are mechanically interconnected. The proximal ends of the internal beam 24 of the first gripping member 14 and of the corresponding internal beam of the second gripping member 15 are not directly connected with the proximal end 21 of the synthetic body 20.

An area on the proximal end of the external beam 23 of the first gripping member 14 or a transition area between the proximal end 21 of the synthetic body 20 on the one hand and the external beam 23 of the first gripping member 14 forms a first solid-state joint 31. An area of the first stud 26 adjoining the external beam 23 of the first gripping member 14 or a transitional area between the first stud 26 and the external beam 23 forms a second solid-state joint 32. An area of the first stud 26 adjoining the internal beam 24 or a transitional area between the first stud 26 and the internal beam 24 forms a third solid-state joint 33. Present on the second stud 27 are corresponding solid-state joints that are not identified with reference numbers of their own. A transitional area between the internal beam 24 of the first gripping member 14 and the corresponding internal beam of the second gripping member 15 forms a fourth solid-state joint 34. Contrary to the depiction in FIG. 1, in the areas of the solid-state joints 31, 32, 33, 34 reduced cross-sections are present in order to localize an elastic reshaping.

A metallic layer 40 is present on the surface of the synthetic body 20. The metallic layer 40 can include a single layer or a multi-layer system made of several partial layers. For example the metallic layer 40 includes a nickel layer with an average granular size of less than 100 nm, in particular with an average granular size in the range of 10 nm to 20 nm, and a copper layer between the synthetic body 20 and the nickel layer.

The metallic layer 40 includes several areas that, as shown in FIG. 1, continue into one another or, contrary to the depiction in FIG. 1, can be severed from one another by gaps. A first portion or area 41 of the metallic layer 40 is present on the external surface of the external beam 23. A second portion or area 42 of the metallic layer 40 is present on the internal surface of the external beam 23. A third portion or area 43 of the metallic layer 40 is present on the external surface of the internal beam 24. A fourth portion or area 44 of the metallic layer 40 is present on the internal surface of the internal beam 24 or on the gripping surface 16 of the first gripping member 14. A fifth portion 45 of the metallic layer 40 is present on the surface of the first stud 26. Corresponding areas of the metallic layer 40 are present on the second stud 27 and on the second gripping member 15.

The synthetic body 20 and the metallic layer 40 are elastically reshapable, in particular in the areas of the solid-state joints 31, 32, 33, 34. Because the synthetic body 22 can comprise greater elasticity than the metallic layer 40, the medical gripping tool 10 can be configured in such a way that in the expected application the synthetic body 20 is reshaped elastically and the metallic layer 40 is reshaped partly only elastically and partly also structurally. In particular, the medical gripping tool 10 can be configured in such a way that the metallic layer 40 is structurally reshaped in the expected application in the areas of the solid-state joints 31, 32, 33, 34.

The medical gripping tool 10 can, in particular, be reshaped in such a way that the gripping members 14, 15 are moved toward one another until the gripping surfaces 16, 17 touch one another or a medical object that is placed between them. For this purpose, the fourth solid-state joint 34 in particular is pulled in the proximal direction between the internal beams 24 of both gripping members 14, 15 by means of a device not shown in FIG. 1. In this way the gripping members 14, 15 can be reshaped according to the fin-ray effect. The medical gripping tool 10 or its gripping members 14, 15 can, in particular, be configured so that, in gripping a convex object, they surround it in each case in an arc shape.

As already mentioned, the metallic layer 40 influences the mechanical properties of the gripping members 14, 15, in particular their elasticity and their reshaping upon gripping a medical object. The metallic layer 40 at the same time influences the mechanical properties of the medical gripping tool 10 at various sites in different ways. Contrary to the illustration in FIG. 1, the metallic layer 40 can comprise various properties in various areas, for example different layer structures, materials, layer thicknesses. In addition, the metallic layer 40 can perform electrical functions and for this purpose can be configured differently in various areas of the medical gripping tool 10.

Additional embodiments of the medical gripping tool 10 are presented hereinafter with reference to FIGS. 2 through 5. In the process, the two gripping members 14, 15 are shown symmetrically in similar manner as in FIG. 1. Contrary to that depiction, however, the two gripping members 14, 15 can differ in configuration with respect to both the synthetic body 20 and the metallic layer 40.

Figure 2:
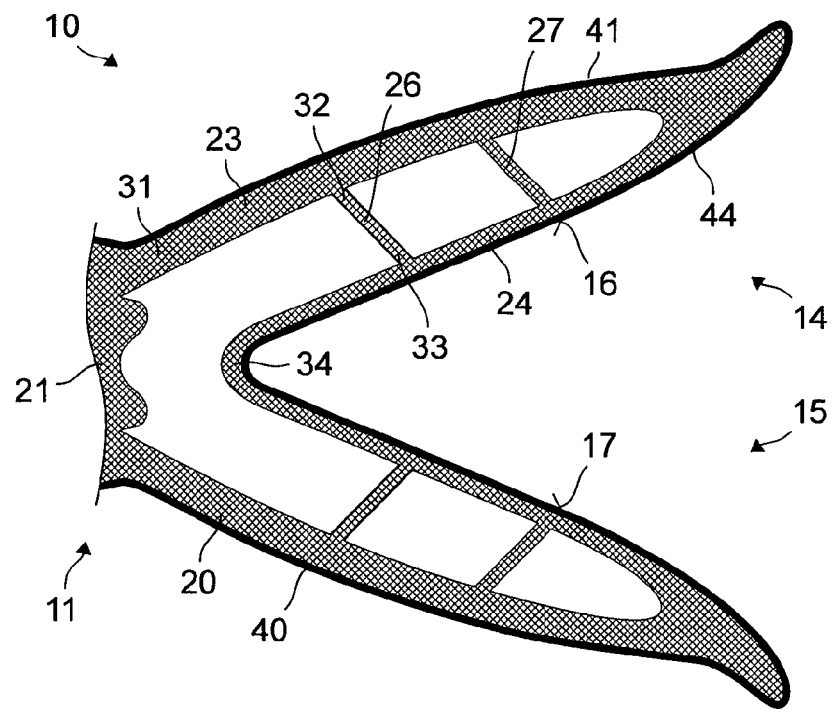
FIG. 2 shows a schematic depiction of another medical gripping tool of an embodiment of the present invention.

FIG. 2 shows a schematic depiction of a medical gripping tool 10, which resembles in some characteristics the medical gripping tool described above with reference to FIG. 1, particularly with respect to the synthetic body 20. However, unlike the medical gripping tool presented above with respect to FIG. 1, in the medical gripping tool 10 shown in FIG. 2 only the first area 41 of the metallic layer 40 on the external surface of the external beam 23 and the fourth area 44 of the metallic layer 40 on the gripping surfaces 16, 17 are present. No metallic layer is present on the internal surface of the external beam 23, on the external surface of the internal beam 24 and on the studs 26, 27. As a result of this configuration of the medical gripping tool 10, it is possible, for example, to generate especially high elasticity of the studs 26, 27 and simultaneously an especially high tractive rigidity of the beams 23, 24.

FIG. 3 shows a schematic depiction of an additional medical gripping tool 10, which resembles in some characteristics the medical gripping tool presented above with reference to FIG. 2. Contrary to the latter, in the medical gripping tool 10 shown in FIG. 3 the metallic layer 40 in the first area 41 on the external surface of the external beam 23 is thicker in configuration than in the fourth area 44 on the internal surface of the internal beam 24. As a result of this configuration, the pliability of the internal beam 24, for example, can be higher or essentially higher than that of the external beam 23. For this purpose, contrary to the depiction in FIG. 3, the metallic layer 40 in the fourth area 44 on the gripping surface 16 can be dispensed with altogether. With the thin metallic layer in the fourth area 44 on the internal surface of the internal beam 24 as shown in FIG. 3, it is possible simultaneously to ensure sufficient elasticity of the internal beam 24 and to allow electrical functionality.

FIG. 4 presents a schematic depiction of an additional medical gripping tool 10, which resembles in some characteristics the medical gripping tool presented above with reference to FIG. 1 and, in particular, the medical gripping tools presented above with reference to FIGS. 2 and 3. Contrary to the medical gripping tools described above with reference to FIGS. 1 through 3, the medical gripping tool 10 in FIG. 4 comprises a metallic layer 40 only on the gripping surfaces 16, 17. This metallic layer 40 in the fourth area 44 on the gripping surfaces 16, 17, in particular, makes possible an electrical functionality and/or a reduced elasticity, in particular a reduced ductility or contractibility, of the internal beam 24.

Contrary to the medical gripping tools described above with reference to FIGS. 1 through 3, the gripping tool illustrated in FIG. 4 in addition comprises an electrical plug-in contact 61 on the distal end 11 and a wire or cord 62. The wire or cord 62 is embedded in the synthetic body 20, in particular molded to it, and connects the electrical plug-in contact 61 by electrically conductive means with the metallic layer 40. For this purpose the wire or cord 62 is situated on the distal end of the gripping member 14 on the gripping surface 16, where it touches the metallic layer 40. In addition, the wire or cord 62 can be configured to influence the mechanical properties of the synthetic body, in particular of the external beam 23.

Figure 5:
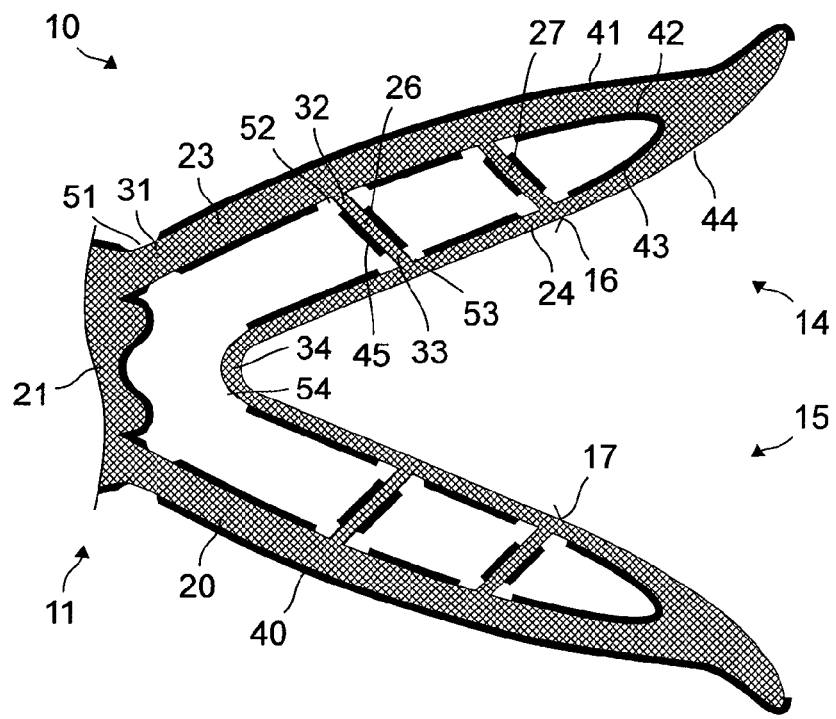
FIG. 5 shows a schematic depiction of another medial gripping tool of an embodiment of the present invention.

FIG. 5 presents a schematic depiction of a medical gripping tool 10 that, in particular, resembles in a few characteristics the medical gripping tool illustrated above in FIG. 1. Contrary to the medical gripping tool illustrated above in FIG. 1, the medical gripping tool 10 of FIG. 5 comprises no metallic layer on the gripping surfaces 16, 17. Alternatively, unlike the depiction in FIG. 5, however, a metallic layer can be present on the gripping surfaces 16, 17, which can be thinner than in the other areas 41, 42, 43, 45.

In addition, the medical gripping tool 10 of FIG. 5 is differentiated from the medical gripping tool illustrated in FIG. 1 in that the metallic layer 40 comprises spaces or gaps 51, 52, 53, 54 in the areas of the solid-state joints 31, 32, 33, 34. As a result, the elasticity of the synthetic body in the areas of the solid-state joints 31, 32, 33, 34 can be maintained without reduction. In other areas, the metallic layer 40 reduces the elasticity of the medical gripping tool 10. As a result, the reshaping of the medical gripping tool 10 is more markedly localized than in the medical gripping tool illustrated in FIG. 1 and more markedly localized than in a medical gripping tool that is entirely without a metallic layer on the areas of the solid-state joints 31, 32, 33, 34. The kinematic properties of the medical gripping tool 10 are therefore better defined or more independent of the forces and moments that occur in gripping a real object.

Figure 6:
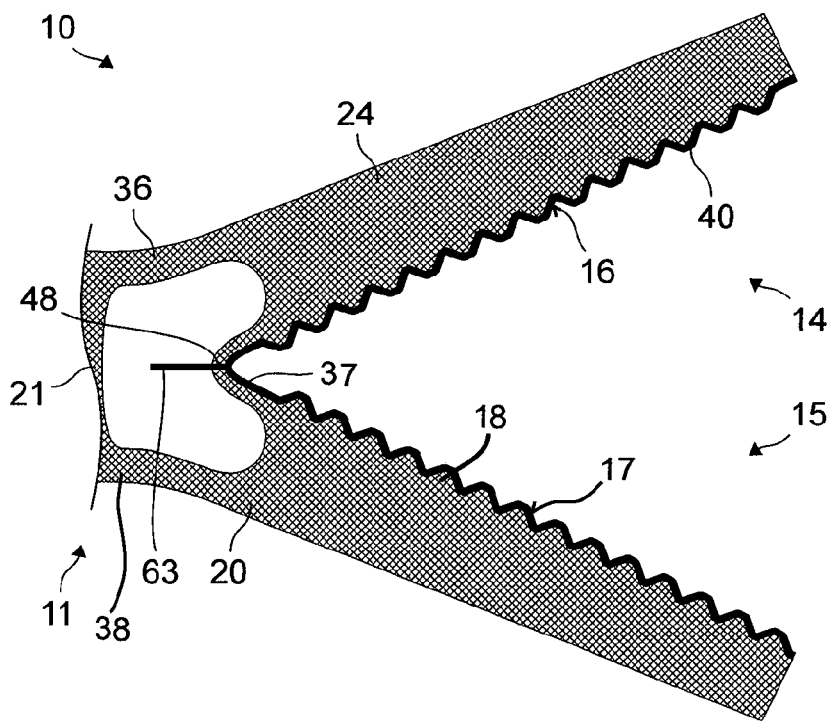
FIG. 6 shows a schematic depiction of another medial gripping tool of an embodiment of the present invention.

FIG. 6 shows a schematic depiction of an additional medical gripping tool 10 with a first gripping member 14 and a second gripping member 15. Contrary to the medical gripping tools presented above with reference to FIGS. 1 through 5, the medical gripping tool 10 shown in FIG. 6 comprises in each case teeth or a cannelure 18. In further contrast to the medical gripping tools in FIGS. 1 through 5, the gripping members 14, 15 of the medical gripping tool 10 shown in FIG. 6 do not comprise a beam structure. On the proximal end the gripping members 14, 15 are interconnected by solid-state joints 36, 37, 38. Because the center solid-state joint 37, which connects the gripping surfaces 16, 17 of the gripping members 14, 15 directly with one another, is pulled in the proximal direction, the gripping members 14, 15 can be moved toward one another.

Similarly as in the medical gripping tool presented above with reference to FIG. 4, only one metallic layer 40 is present on the gripping members 16, 17 of the medical gripping tool 10. This metallic layer 40 can increase the mechanical rigidity of the gripping members 14, 15 and/or make electrical functionality possible. In a departure from the depiction in FIG. 6, the metallic layer can, for example, be present on the entire surface of the gripping members 14, 15 or only on the outsides of the gripping members 14, 15.

The metallic layer 40 is connected in electrically conductive manner with a solder tail 63 by means of a conducting track 48. The conducting track 48 can be a component of the metallic layer 40 and, in particular, can be produced simultaneously with it. The metallic layer can be contacted by the solder tail 63, for example to apply an alternating current of appropriate voltage and amplitude for coagulating tissue.

Figure 7:
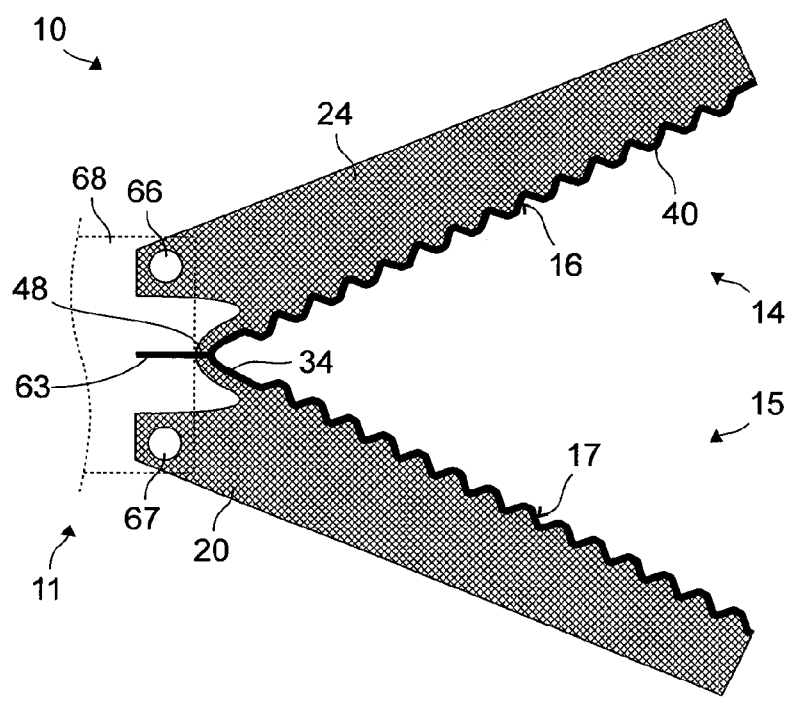
FIG. 7 shows a schematic depiction of another medial gripping tool of an embodiment of the present invention.

FIG. 7 shows a schematic depiction of a medical gripping tool 10, which resembles in a few characteristics the medical gripping tool illustrated above in FIG. 6. Contrary to the medical gripping tool illustrated in FIG. 6, the medical gripping tool of FIG. 7 comprises conventional joints with shafts 66, 67 instead of two solid-state joints. The gripping members 14, 15 are pivotally or rotatably connected by the shafts 66, 67 with a distal end 68 of a shaft of a medical instrument that is only referred to in FIG. 7. The medical gripping tool 10 can be the medical instrument or a part of the medical instrument.

In the medical gripping tool 10 shown in FIG. 7, just as in the gripping tool illustrated above in FIG. 6, the metallic layer 40 is connected in electrically conductive manner with a solder tail 63 by means of a conducting track 48. Each of the two medical gripping tools illustrated in FIGS. 6 and 7 can comprise, instead of a solder tail, an electrical plug-in contact or any other type of contacting device.

Each of the medical gripping tools illustrated in FIGS. 1 through 3 and 5 through 7 can comprise a plug-in contact as illustrated above in FIG. 4, a solder tail as shown in FIGS. 6 and 7, or other contacting devices. In a medical gripping tool that, as shown in FIGS. 1 through 3, comprises a metallic layer extending from the gripping surfaces 16, 17 to the proximal end 11, said metallic layer can be contacted on the proximal end 11, for example by means of a clamp.

The medical gripping tools illustrated above in FIGS. 1 through 5 can comprise cannelures on the gripping surfaces 16, 17, in similar manner as the gripping tools illustrated in FIGS. 6 and 7. The medical gripping tools shown above in FIGS. 6 and 7, similarly as the gripping tools shown in FIGS. 1 through 5, can comprise smooth, or essentially smooth, gripping surfaces 16, 17. In the medical gripping tools shown above in FIGS. 1 through 5, similarly as in the medical gripping tool of FIG. 7, the solid-state joints can be replaced partly by conventional joints with shafts.

Figure 8:
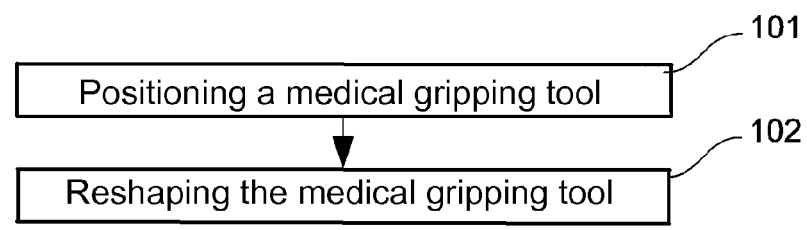
FIG. 8 shows a schematic depiction of a method for handling a medical object.

FIG. 8 shows a schematic flow diagram of a method for handling a medical object. The method can be executed in particular with medical gripping tools as shown above in FIGS. 1 through 7. However, the method can also be executed with medical gripping tools that differ from those shown above in FIGS. 1 through 7. The ensuing use of reference numbers from FIGS. 1 through 7 therefore serves only by way of example for the sake of clarity.

In a first step 101, a medical gripping tool 10 with a synthetic body 20 and a metallic layer 40 on a surface of the synthetic body 20 is positioned on the medical object. In a second step 102, the medical gripping tool is reshaped in order to grip the medical object, whereby the synthetic body is reshaped at least elastically. In this process the metallic layer 40 can be reshaped partly elastically and partly structurally. The reshaping in the second step 102, in particular, is not only inessential, as occurs in particular at solid-state joints. In the second step 102, the gripping tool is reshaped in particular according to the fin-ray effect.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A medical gripping tool comprising:
a synthetic body, the synthetic body is formed with a first gripping member and a second gripping member;
the first gripping member and the second gripping member each having a beam structure, the beam structure being formed by an external beam and an internal beam, the external beam and the internal beam being connected to each other at respective distal ends and separated apart from each other in a proximal direction away from the respective distal ends, the external beams of the first and second gripping members having proximal ends that are connected to each other to form a proximal end of the synthetic body, the internal beams of the first and second gripping members having proximal ends connected to each other without being connected directly to the proximal ends of the external beams, each external beam having an external surface and an internal surface opposite to the external surface; and
a metallic layer disposed on the synthetic body excluding at least a portion of the internal surfaces of the external beams of the first and second gripping members; and
a contacting device for electrically contacting the metallic layer;
wherein the internal beams of the first and second gripping members each has a gripping surface of the gripping tool, the metallic layer includes a portion on the gripping surface, and the portion on the gripping surface is connected with the contacting device in an electrically conductive manner;
wherein the synthetic body includes a solid-state joint between the first gripping member and the second gripping member, the first gripping member and the second gripping member of the synthetic body are reshapable in an expected application of the gripping tool in response to actuation of the gripping tool; and
wherein the metallic layer is structurally reshapable in the expected application.

2. The medical gripping tool of claim 1, wherein at least one of the first gripping member or the second gripping member is configured to be reshaped in accordance with a fin-ray effect upon gripping an object.

3. The medical gripping tool of claim 1, wherein the metallic layer has an average granular size of at most 100 nm.

4. The medical gripping tool of claim 1, wherein the internal beams of the first and second gripping members each comprises a gripping surface of the gripping tool, and wherein the metallic layer is present on the gripping surface.

5. The medical gripping tool of claim 4, wherein the metallic layer is present exclusively on gripping surfaces of the first and second gripping members.

6. The medical gripping tool of claim 1, wherein the internal beams of the first and second gripping members each comprises a gripping surface of the gripping tool, and wherein none of the metallic layer is present on the gripping surface or the metallic layer on the gripping surface is thinner than at other areas of the surface of the synthetic body.

7. The medical gripping tool of claim 1, wherein none of the metallic layer is present on the solid-state joint or the metallic layer at the solid-state joint is thinner than at other areas of the surface of the synthetic body.

8. The medical gripping tool of claim 1, wherein the metallic layer includes a nickel layer, the nickel layer having an average granular size of at most 100 nm; and
a copper layer, the copper layer located between the synthetic body and the nickel layer.

9. The medical gripping tool of claim 1, wherein the beam structure comprises at least one stud extending between the external beam and the internal beam, the at least one stud having ends connected to the external beam and the internal beam by solid-state joints.

10. The medical gripping tool of claim 9, wherein the beam structure comprises multiple studs, the studs being parallel to each other.

11. The medical gripping tool of claim 9, wherein the metallic layer is present on the at least one stud.

12. The medical gripping tool of claim 9, wherein the at least one stud has a reduced cross section at least one of the solid-state joints to provide localized reshaping of the synthetic body.

13. The medical gripping tool of claim 9, wherein the metallic layer comprises gaps at at least one of the solid-state joints.

14. The medical gripping tool of claim 9, wherein the synthetic body is a single piece structure.

15. A method for handling an object, having the following steps: using a medical gripping tool having:
- a synthetic body and a metallic layer on a surface of the synthetic body,
- the synthetic body is formed with a first gripping member and a second gripping member, the first gripping member or the second gripping member each having a beam structure, the beam structure being formed by an external beam and an internal beam,
- the external beam and the internal beam being joined to each other at respective distal ends and being separated apart from each other in a proximal direction away from the respective distal ends, the external beams of the first and second gripping members having proximal ends that are connected to each other to form a proximal end of the synthetic body, the internal beams of the first and second gripping members having proximal ends connected to each other without being connected directly to the proximal ends of the external beams, each external beam having an external surface and an internal surface opposite to the external surface,
- the metallic layer is excluded from at least a portion of the internal surfaces of the external beams of the first and second gripping members, and
- a contacting device for electrically contacting the metallic layer,
- wherein the internal beams of the first and second gripping members each has a gripping surface of the gripping tool, the metallic layer includes a portion on the gripping surface, and the portion on the gripping surface is connected with the contacting device in an electrically conductive manner, and wherein the synthetic body includes a solid-state joint between the first gripping member and the second gripping member;
- Positioning on the object the first gripping member and the second gripping member;
- reshaping the first gripping member and the second gripping member of the medical gripping tool by actuating the gripping tool in order to grip the object, such that the synthetic body is elastically reshaped; and wherein, upon reshaping the medical gripping tool, the metallic layer is structurally reshaped.

\* \* \* \* \*